United States Patent
Park et al.

(10) Patent No.: US 10,034,903 B2
(45) Date of Patent: Jul. 31, 2018

(54) BACTERIUM-BASED MICROROBOT CAPABLE OF TARGETING CANCER TISSUE

(71) Applicant: Industry Foundation of Chonnam National University, Gwangju (KR)

(72) Inventors: Suk Ho Park, Gwangju (KR); Jong Oh Park, Gyeonggi-do (KR); Sung Jun Park, Gwangju (KR); Seong Young Ko, Seoul (KR); Jung Joon Min, Gwangju (KR); Seung Hwan Park, Gwangju (KR)

(73) Assignee: INDUSTRY FOUNDATION OF CHONNAM NATIONAL UNIVERSITY, Gwangju (KR)

( * ) Notice: Subject to any disclaimer, the term of this patent is extended or adjusted under 35 U.S.C. 154(b) by 510 days.

(21) Appl. No.: 13/952,711

(22) Filed: Jul. 29, 2013

(65) Prior Publication Data
US 2014/0037553 A1 Feb. 6, 2014

(30) Foreign Application Priority Data
Jul. 27, 2012 (KR) .................. 10-2012-0082536

(51) Int. Cl.
| | |
|---|---|
| *A61K 9/14* | (2006.01) |
| *A61K 35/74* | (2015.01) |
| *A61K 49/00* | (2006.01) |
| *A61K 47/69* | (2017.01) |

(52) U.S. Cl.
CPC .......... *A61K 35/74* (2013.01); *A61K 47/6901* (2017.08); *A61K 47/6925* (2017.08); *A61K 49/0032* (2013.01); *A61K 49/0091* (2013.01); *A61K 49/0097* (2013.01); *Y02A 50/473* (2018.01); *Y02A 50/481* (2018.01)

(58) Field of Classification Search
CPC .......... A61K 9/14; A61K 9/141; A61K 9/143; A61K 9/145; A61K 9/16; A61K 9/1605
USPC .................................................. 424/489–495
See application file for complete search history.

(56) References Cited

U.S. PATENT DOCUMENTS

2006/0073333 A1 * 4/2006 Anderson .............. A01N 25/26
428/402.2

FOREIGN PATENT DOCUMENTS

| KR | 1020090081758 A | * | 7/2009 | ............... A61K 9/14 |
| KR | 1020090081758 A | | 7/2009 | |
| KR | 1020110093324 A | * | 8/2011 | ............... A61K 9/14 |
| KR | 1020110093324 A | | 8/2011 | |

* cited by examiner

*Primary Examiner* — Micah Paul Young
(74) *Attorney, Agent, or Firm* — Stuart H. Mayer; Mayer & Williams PC

(57) ABSTRACT

To provide a bacterium-based microrobot which can be specifically targeted to cancer in vivo, the present invention provides a drug delivery system for cancer tissue, comprising a bacterium, and a microbead encapsulated with at least one drug, wherein biotin is bound to a surface of the bacterium and a surface of the microbead is coated with streptavidin.

14 Claims, 15 Drawing Sheets

The cell lines were cultured by using 3D alginate gel
(a: NIH3T, b: CT-26 (colon cancer), c: 4T1 (breast cancer)

Tumor targeting of Bacteria in microchamber using 3D cultured cells

Tumor targeting of Bacteriobot in microchamber using 3D cultured cells

BACTERIUM-BASED MICROROBOT CAPABLE OF TARGETING CANCER TISSUE

CROSS-REFERENCE TO RELATED APPLICATION

This application claims priority to Korean Patent Application No. 2012-0082536 filed on Jul. 27, 2012 and all the benefits accruing therefrom under 35 U.S.C. § 119, the contents of which are incorporated by reference in their entirety.

BACKGROUND

The present invention relates to a bacterium-based microrobot, and more particularly, to a cancer tissue targeting bacterium-based microrobot.

A bacterium-based microrobot is a novel concept of a drug delivery system first developed by the present inventers, wherein the bacterium-based microrobot has a structure on which bacteria are adhered to a portion of a surface of microstructure having a size ranging from several μm to several hundreds of μm, and the bacterium-based microrobot can treat diseases by transferring the microstructure to a lesion using a flagellar movement and a disease targeting ability of the bacterium and using a drug and/or a bacterium for treating diseases which are encapsulated in the microstructure (see Korean Patent No. 1003149).

To produce the bacterium-based microrobot having a spherical microstructure, a technique for selectively adhering bacteria to a specific region of the surface of the microstructure is used. Korean Patent Publication No. 2011-0093324 discloses a method of producing a microstructure by using a hydrophobic material for one side of a hemisphere, and a hydrophilic material for the other side of the hemisphere, wherein bacteria are likely to adhere well to the hydrophobic material and bacteria are not likely to adhere to the hydrophilic material. Also, another technique has been known in which bacteria adhere only to a specific hemisphere by surface-treating the specific hemisphere after producing a microstructure using a single material.

SUMMARY

However, there are several drawbacks in the first and second techniques above. That is, in the first technique, production is not easy due to repulsion between a hydrophilic material and a hydrophobic material, and in the second method, the process is complicate and has a low yield.

To overcome various problems including the problems as mentioned above, the present invention provides a bacterium-based microrobot in which bacteria adhere to a surface of a microbead using binding affinity between streptavidin and biotin. However, this object is merely illustrative, and the scope of the present invention is not limited thereto.

In accordance with an aspect of the present invention, a drug delivery system for cancer tissue, comprising at least a bacterium, and a microbead encapsulating at least a drug, wherein at least a biotin is bound to a surface of the bacterium and a surface of the microbead is coated with streptavidin, and wherein the bacterium is bound to the microbead through an interaction between the biotin and the streptavidin is provided.

In accordance with the drug delivery system, the bacterium may be *Salmonella, Clostridium, Bifidobacterium, E. coli, Yersini. enterocohtica, Listeria monocytogenies, Mycoplasma hominis*, or *Streptococcus*. Preferably, the bacterium may be *Salmonella*, such as *Salmonella typhimurium, Salmonella choleraesuis*, or *Salmonella enteritidis*, and more preferably *Salmonella typhimurium*.

Also, in accordance with the drug delivery system, the bacterium may be a mutant lack of an ability to synthesize guanosine 5'-diphosphate 3'-diphosphate (ppGpp), and the bacterium may include an inactivated relA gene and/or spoT gene which encode ppGpp synthease for ppGpp synthesis.

Also, the bacterium may be an attenuated bacterium.

Also, the cancer may be any one selected from the group consisting of liver cancer, colorectal cancer, cervical cancer, renal cancer, gastric cancer, prostate cancer, breast cancer, brain tumor, lung cancer, uterine cancer, colon cancer, bladder cancer, hematologic malignancy and pancreatic cancer.

Also, the drug may be a marker gene, a chemical material, a peptide, a polypeptide, a nucleic acid, carbohydrate or lipid and may be a marker gene. The marker gene may be a gene encoding a fluorescence protein or a luminescence protein, or a gene encoding a marker for nuclear medicine or MRI imaging including thymidine kinase of herpes simplex virus, a dopamine receptor, a somatostatin receptor, a sodium-iodide transporter, an iron receptor, a transferrin receptor, ferritin or an iron transporter (magA). Also, the chemical material may be an anti-cancer drug and one or more selected from doxorubicin, epirubicin, cisplatin, carboplatin, oxaliplatin, paclitaxel, docetaxel, 5-fluorouracil, cytarabine, gemcitabine, pentostatin, methotrexate, 7-ethyl-10-hydroxycamptothecin, trimetrexate, vinblastine, vincristine and dexamethasone.

Also, the drug may be chemotherapeutic agents, and the bacterium may be genetically modified to produce the drug.

Also, the microbead may be produced by using a biodegradable/biocompatible polymer material, and the microbead may include a drug capsule or a bacterial capsule which are produced by using a biodegradable/biocompatible polymer material.

The biodegradable/biocompatible polymer material may be one or more selected from chitosan, a salt and a derivative thereof; dextran and a derivative thereof; gum acacia; tragacanthin; hyaluronic acid, a salt and a derivative thereof; pectin, a salt and a derivative thereof; alginic acid, a salt and a derivative thereof; agar; galactomannan, a salt and a derivative thereof; xanthan, a salt and a derivative thereof; β-cyclodextrin, a salt and a derivative thereof; amylose (water soluble starch), a salt and a derivative thereof; glycol chitosan, a salt and a derivative thereof; carboxylmethyl cellulose (CMC), a salt and a derivative thereof; hydroxyethyl cellulose (HEC), a salt and a derivative thereof; hyroxypropyl methyl cellulose (HPMC), a salt and a derivative thereof; methyl cellulose, a salt and a derivative thereof; cellulose acetate phthalate, a salt and a derivative thereof; gelatin, a salt and a derivative thereof; promaine sulfate; poly(β-hydroxyethyl methacrylate) (PHEMA); polyacrylamide (PA); polyvunyl alcohol (PVA); polyacrylic acid (PAA); polyethylene gylcol (PEG); poly(ethylene oxide-b-propylene oxide) (PER-PPO); and polylyasine.

In accordance with the drug delivery system, the diameter of the microbead may be 5 μm or less and raging from 1 to 5 μm.

In accordance with another aspect of the present invention, a pharmaceutical composition for treating cancer is provided, wherein the pharmaceutical composition for treating cancer including: (a) a pharmaceutically effective dose of the drug delivery system described above; and (b) a pharmaceutically acceptable carrier, wherein, the drug delivery system is characterized by including a drug for treating cancer.

In accordance with another aspect of the present invention, a composition for imaging cancer is provided, wherein the composition for imaging cancer including: (a) the drug delivery system described above; and (b) a pharmaceutically acceptable carrier.

In accordance with another aspect of the present invention, a method for delivering a drug to cancer tissue is provided, the method including a step of administering a drug delivery system for cancer tissue to a subject, wherein the drug delivery system includes a bacterium and a microbead, wherein at least one biotin is bound to a surface of the bacterium and a surface of the microbead is coated with streptavidin.

In accordance with the method for delivering a drug to cancer tissue, the bacterium may be *Salmonella, Clostridium, Bifidobacterium, E. coli, Yersinia. enterocohtica, Listeria monocytogenies, Mycoplasma hominis*, or *Streptococcus*, and preferably the bacterium may be *Salmonella*. The bacterium may be *Salmonella typhimurium, Salmonella choleraesuis*, or *Salmonella enteritidis*, and more preferably *Salmonella typhimurium*.

Also, in accordance with the method, the bacterium may be a mutant lack of an ability to synthesize ppGpp, and the bacterium may include an inactivated relA gene and/or spoT gene which encode ppGpp synthease for ppGpp synthesis.

Also, the bacterium may be an attenuated bacterium.

Also, the cancer may be any one selected from the group consisting of liver cancer, colorectal cancer, cervical cancer, renal cancer, gastric cancer, prostate cancer, breast cancer, brain tumor, lung cancer, uterine cancer, colon cancer, bladder cancer, hematologic malignancy and pancreatic cancer.

Also, the drug may be a marker gene, a chemical material, a peptide, a polypeptide, a nucleic acid, carbohydrate or lipid.

Also, the marker gene may be a gene encoding a fluorescence protein or a luminescence protein, or a gene encoding a marker for nuclear medicine or MRI imaging including thymidine kinase of herpes simplex virus, a dopamine receptor, a somatostatin receptor, a sodium-iodide transporter, an iron receptor, a transferrin receptor, ferritin or an iron transporter (magA).

Also, the chemical material may be an anti-cancer drug and one or more selected from doxorubicin, epirubicin, cisplatin, carboplatin, oxaliplatin, paclitaxel, docetaxel, 5-fluorouracil, cytarabine, gemcitabine, pentostatin, methotrexate, 7-ethyl-10-hydroxycamptothecin, trimetrexate, vinblastine, vincristine and dexamethasone.

Also, the drug may be chemotherapeutic agents, and the bacterium may be genetically modified to produce the drug.

Also, the microbead may be produced by using a biodegradable/biocompatible polymer material, and the microbead may include a drug capsule or a bacterial capsule which are produced by using a biodegradable/biocompatible polymer material. The biodegradable/biocompatible polymer material may be one or more selected from chitosan, a salt and a derivative thereof; dextran and a derivative thereof; gum acacia; tragacanthin; hyaluronic acid, a salt and a derivative thereof; pectin, a salt and a derivative thereof; alginic acid, a salt and a derivative thereof; agar; galactomannan, a salt and a derivative thereof; xanthan, a salt and a derivative thereof; β-cyclodextrin, a salt and a derivative thereof; amylose (water soluble starch), a salt and a derivative thereof; glycol chitosan, a salt and a derivative thereof; carboxylmethyl cellulose (CMC), a salt and a derivative thereof; hydroxyethyl cellulose (HEC), a salt and a derivative thereof; hyroxypropyl methyl cellulose (HPMC), a salt and a derivative thereof; methyl cellulose, a salt and a derivative thereof; cellulose acetate phthalate, a salt and a derivative thereof; gelatin, a salt and a derivative thereof; promaine sulfate; poly(β-hydroxyethyl methacrylate) (PHEMA); polyacrylamide (PA); polyvunyl alcohol (PVA); polyacrylic acid (PAA); polyethylene gylcol (PEG); poly (ethylene oxide-b-propylene oxide) (PER-PPO); and polylyasine.

The method may include administering the drug intravenously.

In accordance with another aspect of the present invention, a method for treating cancer is provided, wherein the method for treating cancer including a step of administrating a pharmaceutical composition having: (a) a pharmaceutically effective dose of the drug delivery system described above; and (b) a pharmaceutically acceptable carrier, wherein, the drug delivery system is characterized by including a drug for treating cancer.

In accordance with still another aspect of the present invention, a composition for imaging cancer is provided, wherein the composition for imaging cancer including a step of administering a pharmaceutical composition having: (a) the drug delivery system described above; and (b) a pharmaceutically acceptable carrier.

BRIEF DESCRIPTION OF THE DRAWINGS

Exemplary embodiments can be understood in more detail from the following description taken in conjunction with the accompanying drawings, in which.

DETAILED DESCRIPTION OF EMBODIMENTS

Figure 1:
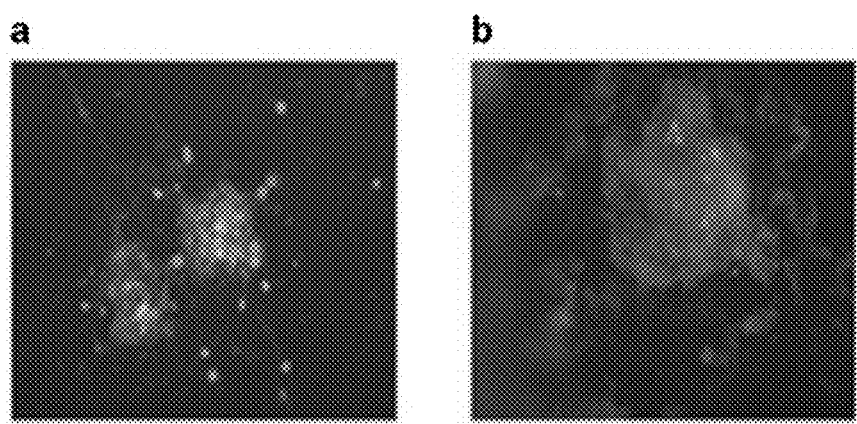
FIGS. 1A and 1B are photographs of an immunostaining result verifying an anti-cancer effect of a *S. typhimurium* strain (ΔppGpp) which is used for a bacterium-based microrobot according to an example of the present invention.

The terms used herein are defined as follows.

As used herein a "drug delivery system" means a bacterium-based microrobot to which at least on attenuated bacterium is bound to a microbead, wherein the microbead is produced by using a biodegradable/biocompatible polymer material. The attenuated bacterium is characterized in that a plurality of OmpA proteins presented on a surface of the bacterium is bounded to biotin through a covalent bond. Also, a surface of the microbead is coated with streptavidin thus maintaining the binding in vivo through streptavidin-biotin binding affinity, and providing an anti-cancer effect by migrating in a cancer tissue specific manner. Through an example of the present invention, it is verified that the drug delivery system can maintain the binding strongly in vivo, and can provide a cancer tissue targeting effect.

As used herein "attenuation" means modifying a microorganism so as to reduce pathogenicity. Attenuation is performed for the purpose of reducing toxicity and other side effects in the case where the microorganism is administered to patients. The attenuated bacterium is produced by using various methods known in the art. For example, attenuation is achieved by deleting or disrupting a virulence factor, which helps the bacterium to survive in a host cell. The deletion and disruption have been well known in the art, and are performed through methods such as a homologous recombination, chemical mutagenesis, irradiation mutagenesis, or transposon mutagenesis. Examples of virulence factors of *Salmonella* which cause attenuation in the case of deletion are as follows: 5'-adenosine monophospate (Biochenko et al., 1987, *Bull. Eksp. Biol. Med.* 103: 190-192), cytolysin (Libby et al., 1994, *Proc. Natl. Acad. Sci. USA* 91: 489-493), defensin tolerance loci (Fields et al., 1989, *Science* 243: 1059-62), DNAK (Buchmeier et al., 1990, *Science* 248: 730-732), fimbriae (Ernst et al., 1990, *Infect. Immun.* 58: 2014-2016), GroEL (Buchmeier et al., 1990, *Science* 248: 730-732), Inv loci (Ginocchio et al., 1992, *Proc. Natl. Acad. Sci. USA* 89: 5976-5980), lipoprotein (Stone et al., 1992, *J. Bacteriol.* 174: 3945-3952), LPS (Gianella et al., 1973, *J. Infect. Dis.* 128: 69-75), PhoP and PhoQ (Miller et al., 1989, *Proc. Natl. Acad. Sci. USA* 86: 5054-5058), a Pho activating gene (Abshiro et al., 1993, *J. Bacteriol.* 175: 3734-3743), a PhoP and PhoQ regulatory gene (Behlau et al., 1993, *J. Bacteriol.* 175: 4475-4484), porine (Tufano et al., 1988, *Eur. J. Epiderniol.* 4: 110-114), and a virulence factor (Loos et al., 1994, *Immun. Infekt.* 22: 14-19; Sansonetti, 1992, *Rev. Prat.* 42: 2263-2267). The attenuated bacterium is disclosed in WO 96/40238 in detail, and this patent document is incorporated herein by reference.

As used herein, "an inactivated relA gene and/or a spoT gene" means modifications in a relA gene and/or a spoT gene which cause impairment of transcription or translation of a gene or impairment of activation of a gene product. The gene modification may include inactivation of a ppGpp synthetase coding sequence (CDS) as well as inactivation of the promoter of CDS. The specific inactivation of only a desired gene on a bacterial genome can be achieved by mutating a whole coding gene or at least one partial region of a coding gene through substitution, insertion, deletion, or a combination thereof. For example, the deletion of a gene and the insertion of a heterogenous sequence into a gene may cause truncation of a gene, nonsense mutation, frameshift mutation, missense mutation, etc. The specific inactivation of a gene can be performed by a method established in the art. Whereas, a deletion of a gene can be performed through a various mutagenesis method known in the art. For example, a deletion of relA gene and/or spoT gene can be performed through PCR mutagenesis and cassette mutagenesis (Sambrook, J. et al., Molecular Cloning. A Laboratory Manual, 3rd ed. Cold Spring Harbor Press (2001)). Deficiency in ppGpp synthesis crucially contributes to cancer tissue targeting of the bacterium of the present invention.

As used herein, a "chemical material" of the drug delivery system has a comprehensive meaning that the chemical material is included in a cancer-targeting bacterial cell and also genes which allow the cancer-targeting bacterium to produce the chemical material are included.

As used herein, "a peptide or a polypeptide" of the drug delivery system has a comprehensive meaning that the peptide or the polypeptide is included in the cancer-targeting bacterial cell and also genes which allow the cancer-targeting bacterium to produce the peptide or the polypeptide are included. For example, the cancer-targeting bacterium of the present invention may include a heterogous gene encoding a protein which is useful for treatment of a cancer, siRNA, or shRNA, and in this case, the cancer-targeting bacterium acts as a gene therapeutic agent.

Preferably, a "nucleic acid" molecule of the drug delivery system as used herein operatively linked to a promoter, which is operated in the cancer-targeting bacterium. The term "operatively linked to" means a functional binding between a regulatory sequence of nucleic acid expression (for example, a promoter, a signal sequence, or an array of a transcription regulatory factor binding site) and other nucleic acid sequences, and the regulatory sequence thus regulates a transcription and/or translation of the other nucleic acid sequences. A nucleic acid to be transported may be transported by constructing a vector system, and the vector system can be constructed through various methods known in the art. The detailed methods for constructing the vector system are disclosed in Sambrook et al., *Molecular Cloning, A Laboratory Manual*, Cold Spring Harbor Laboratory Press (2001), and this document is incorporated herein by reference. For example, a vector generally includes a promoter which can initiate a transcription (for example, tac promoter, lac promoter, lacUV5 promoter, lpp promoter, pLλ promoter, pRλ promoter, rac5 promoter, amp promoter, recA promoter, SP6 promoter, trp promoter, T7 promoter, pBAD promoter, Tet promoter, trc promoter, pepT promoter, sulA promoter, pol II(dinA) promoter, ruv promoter, uvrA promoter, uvrB promoter, uvrD promoter, umuDC promoter, lexA promoter, cea promoter, caa promoter, recN promoter and pagC promoter), a ribosome binding site for initiating translation, and a terminal sequence of transcription/translation (for example, rrnB terminator). In addition, a promoter, which is selectively expressed in a cancer tissue, is also included. Meanwhile, a vector, which can be used in the present invention, may be produced by manipulating plasmids often used in the art (for example, pSC101, pGV1106, pACYC177, ColE1, pKT230, pME290, pBR322, pUC8/9, pUC6, pBD9, pHC79, pIJ61, pLAFR1, pHV14, pGEX series, pET series and pUC19), phages (for example, λgt4λB, λ-Charon, λz1, and M13) or viruses (for example, SV40).

Also, the heterogous nucleic acid may further include a leader sequence (or a signal sequence), in order for a protein expressed by the heterogous nucleic acid used herein to be easily secreted outside cells. The leader sequence appropriate for the present invention is not particularly limited and may further include a leader sequence such as pelB, ompA, ompB, ompC, ompD, ompE, ompF, ompT, phoA, and phoE.

Also, the nucleic acid molecule transported by the cancer-targeting bacterium of the present invention may be transported through transposon-mediated chromosomal integration. In this case, a transposon plasmid is used and the plasmid includes a transposon into which the target nucleic acid molecule is integrated. This transposon is integrated into the bacterial genome. An example of suitable transposon includes TO, Tn9, Tn1O, and Tn5, but is not limited thereto.

As used herein, an "effective dose" means a sufficient dose for exhibiting a therapeutic efficacy of the present invention stated above.

As used herein, a "pharmaceutically acceptable carrier" is commonly used for preparation, and includes a carbohydrate-based compound (for example, lactose, amylose, dextrose, sucrose, sorbitol, mannitol, starch, and cellulose), gum acacia, calcium phosphate, alginate, gelatin, calcium silicate, microcrystalline cellulose, polyvinylpyrrolidone, water, syrup, a salt solution, alcohol, gum arabic, vegetable oil (for example, corn oil, cottonseed oil, soybean oil, olive oil, and coconut oil), polyethylene glycol, methyl cellulose, methyl hydroxybenzoate, propyl hydroxybenzoate, talc, magnesium stearate and mineral oil, but is not limited thereto. A pharmaceutical composition of the present invention may further include a lubricant, a humectant, a sweeting agent, a favoring agent, an emulsifier, a suspension, and a preservate besides the above components. An appropriate preparation and pharmaceutically acceptable carrier are disclosed in Remington's Pharmaceutical Sciences (19$^{th}$ ed., 1995) in detail.

The pharmaceutical composition is preferably administered parenterally, and in the case of parenteral administration, the pharmaceutical composition may be administered through intravenous injection, subcutaneous injection, intramuscular injection, intraperitoneal injection, etc.

An appropriate dose of the pharmaceutical composition depends on factors such as a preparation method, administration type, age, weight, sex, and a disease state of a patient, food, time of administration, route of administration, excretion rate, and susceptibility to the reaction. A skilled practitioner can easily determine and prescribe a dosage effective for the desired treatment or prevention. According to a preferred embodiment of the present invention, an appropriate daily dose is 0.0001 to 100 mg/kg (weight). Administration can be done once a day or can be divided several times during a day.

Also, the pharmaceutical composition according to an example of the present invention may be prepared in a unit dosage form or prepared as being encapsulated in a capacity container, by using a pharmaceutically acceptable carrier and/or excipient, according to a method which can be easily performed by a person skilled in the art. In this case, the formulation may be in the form of oil, a solution having aqueous solvent, a suspension, an emulsion, an extract, granules, a tablet, or a capsule, and may further include a dispersing agent or a stabilizer.

As used herein a "composition for imaging" is used for imaging cancer by being applied to various methods of imaging a marker. For example, in the case where a maker is composed of a magnetic material, magnetic resonance (MR) may be used, and in the case where a maker is a positron emission isotope, single photon emission computed tomography (SPECT), or positron emission tomography (PET) may be used. The MR imaging method and device are disclosed in following disclosure: D. M. Kean and M. A. Smith, Magnetic Resonance Imaging: Principles and Applications (William and Wilkins, Baltimore 1986); U.S. Pat. No. 6,151,377, U.S. Pat. No. 6,144,202, U.S. Pat. No. 6,128,522, U.S. Pat. No. 6,127,825, U.S. Pat. No. 6,121,775, U.S. Pat. No. 6,119,032, U.S. Pat. No. 6,115,446, and U.S. Pat. No. 6,111,410. The PET imaging method and device are disclosed in U.S. Pat. No. 6,151,377, U.S. Pat. No. 6,072,177 U.S. Pat. No. 5,900,636, U.S. Pat. No. 5,608,221, U.S. Pat. No. 5,532,489, U.S. Pat. No. 5,272,343 and U.S. Pat. No. 5,103,098, and these patent documents are incorporated herein by reference. The SPECT imaging method and device are disclosed in U.S. Pat. No. 6,115,446, U.S. Pat. No. 6,072,177, U.S. Pat. No. 5,608,221, U.S. Pat. No. 5,600,145, U.S. Pat. No. 5,210,421, and U.S. Pat. No. 5,103,098, and the patent documents are incorporated herein by reference. In the case where a marker is a luminescence material, a fluorescence material, or a chemiluminescence material, an image of cancer tissue may be obtained through optical imaging and spectroscopy. A general description about the imaging is disclosed in U.S. Pat. No. 5,650,135. Also, in the case where a marker is bound to barium sulphate and iodine, which are X-ray contrast media, or in the case where a marker is a microbubble, which is a contrast agent for ultrasonography, the marker may also be used in X-ray and ultrasonography.

As used herein "cancer treating method" means a method including a step of administrating a pharmaceutical composition having a pharmaceutically effective dose of the drug delivery system and a pharmaceutically acceptable carrier to a subject, wherein a drug for the cancer treatment is included in the drug delivery system. The treatment may simply be terminated by injecting an antibiotic. An example of the antibiotic, which may be used, includes ciprofloxacin, ampicillin, gentamycin, carbenicillin, chloramphenicol, streptomycin, kanamycin, geneticin, neomycin and tetracycline, but is not limited thereto.

Hereinafter, the present invention will be described through examples and experimental examples. However, the present invention is not limited to the examples and experimental examples disclosed hereinafter, and may be implemented in various formed different from each other. The examples and experimental examples hereinafter are provided for completing the present invention, and for completely enlightening contents of the present invention to a person skilled in the art.

FIG. 1 is a photograph of an immunostaining result verifying an anti-cancer effect of a *S. typhimurium* strain (ΔppGpp) which is used for a bacterium-based microrobot according to an example of the present invention. To verify the anti-cancer effect of the *S. typhimurium* strain (ΔppGpp), the *S. typhimurium* strain (ΔppGpp) was loaded on an alginate hydrogel bead including a colorectal cancer cell CT-26, a breast cancer cell 4T1, and a NIH3T3 cell, and then immunostaining was performed using an anti-EthD-1 antibody which specifically stains a dead cell. As a result, only the alginate hydrogel including the colorectal cancer cell or the breast cancer cell was stained in red, and thus the cancer cell killing effect of the strain was verified.

Figure 2A:
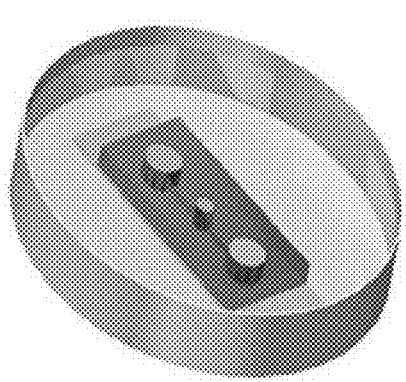
FIG. 2 illustrates a 3-chamber produced for determining chemotaxis, toward cancer, of the *S. typhimurium* strain (ΔppGpp) used for the bacterium-based microrobot according to an example of the present invention (FIG. 2A), normal operability of the chamber (FIG. 2B), and chemotaxis of the *S. typhimurium* strain (ΔppGpp) toward cancer (FIG. 2C), and of the bacterium-based microrobot (FIG. 2D)
Figure 2A:
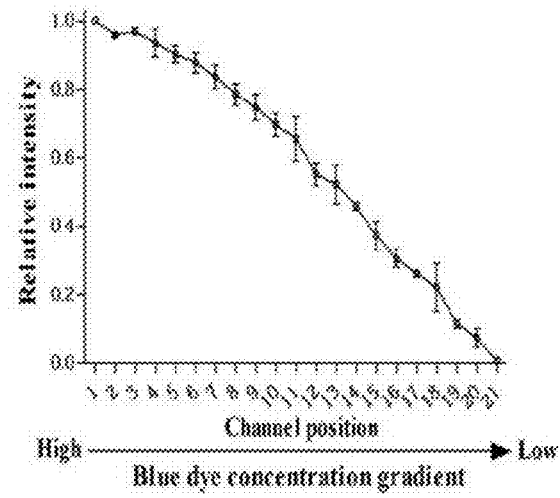
Figure 2B:
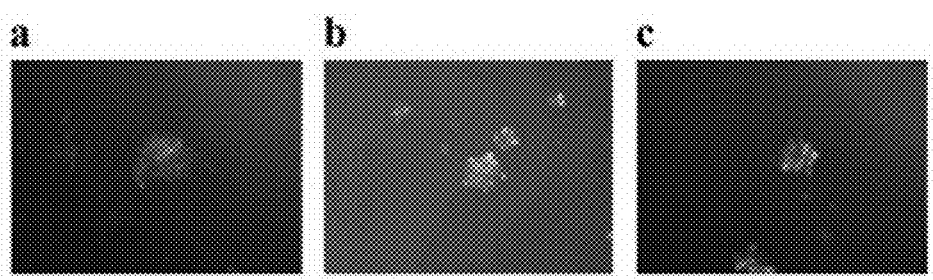
Figure 2C:
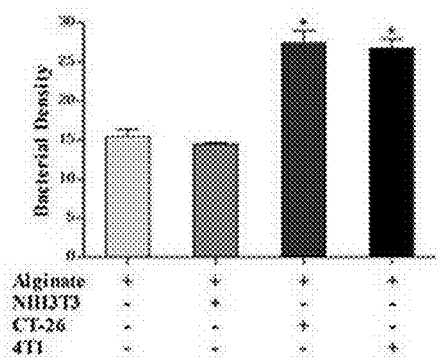
Figure 2D:
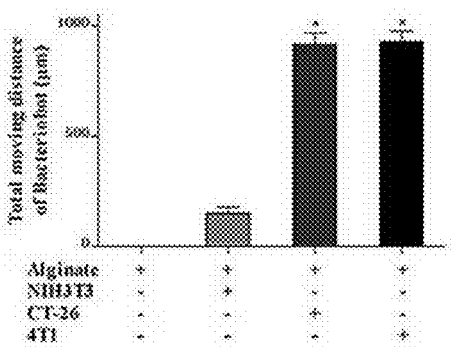

FIG. 2 illustrates a 3-chamber produced for verifying chemotaxis, toward cancer, of the *S. typhimurium* strain (ΔppGpp) used for the bacterium-based microrobot according to an example of the present invention (FIG. 2A), normal operability of the chamber (FIG. 2B), and chemotaxis of the *S. typhimurium* strain (ΔppGpp) toward cancer (FIG. 2C), and of the bacterium-based microrobot (FIG. 2D). The present inventor verified chemotaxis of the *S. typhimurium* strain (ΔppGpp) toward cancer using a 3-chamber which has been developed through the previous study of the present inventor in order to verify cancer-specific chemotaxis of the *S. typhimurium* strain (ΔppGpp). As a result, it was verified that a migration toward the colorectal cancer cell and the breast cancer cell is preferred.

Figure 3:
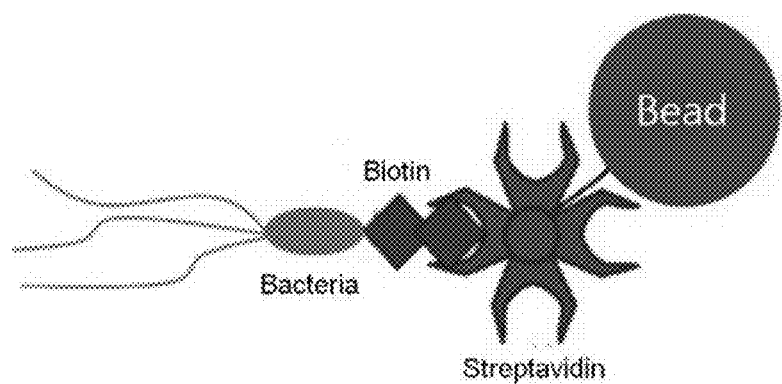
FIG. 3 is a schematic diagram illustrating the bacterium-based microrobot according to an example of the present invention.

FIG. 3 is a schematic diagram illustrating the bacterium-based microrobot according to an example of the present invention.

FIG. 4 illustrates fluorescence (FIG. 4A) and near-infrared (FIG. 4B) in an animal model which is administered with the bacteria (the *S. typhimurium* strain (ΔppGpp)), or a microbead, according to an example of the present invention, and also illustrates fluorescence (FIG. 4C) and near-infrared (FIG. 4D) in an animal model which is administered with the bacterium-based microrobot. To verify chemotaxis toward cancer, of the bacterium-based microrobot according to an example of the present invention in vivo, an animal model of cancer was used. The *S. typhimurium* strain (ΔppGpp), the microbead, or the bacterium-based microrobot was administered, respectively, through tail vein of the animal model of cancer. Three days after administration, locations of the *S. typhimurium* strain (ΔppGpp) and the microbead were checked by measuring fluorescence and near-infrared. As a result, fluorescence of the *S. typhimurium* strain (ΔppGpp) was observed in cancer tissue, however, near-infrared was not observed in cancer tissue due to the lack of motility of the microbead. The migration of near-infrared of the bacterium-based microrobot to a cancer tissue was not observed due to interference caused by auto-fluorescence.

Figure 4A:
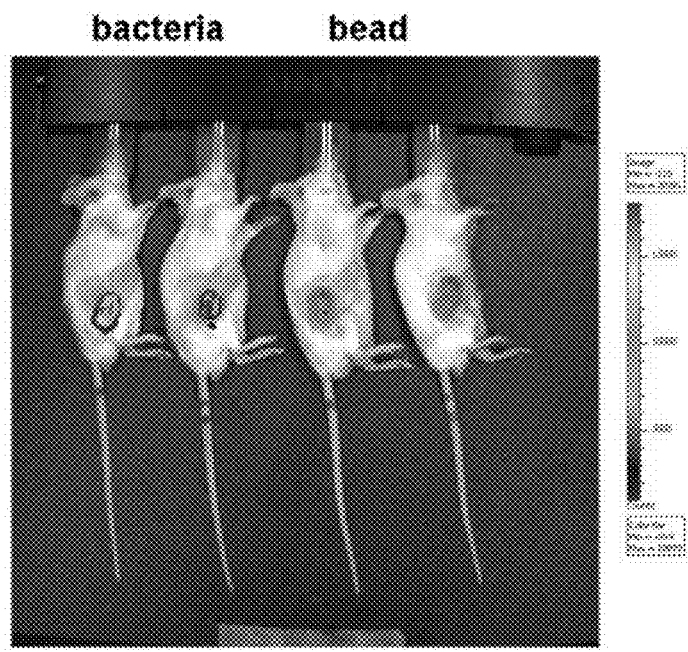
FIG. 4 illustrates fluorescence (FIG. 4A) and near-infrared (FIG. 4B) in an animal model which is administered the bacteria (the *S. typhimurium* strain (ΔppGpp)), or a microbead, according to an example of the present invention, and also illustrates fluorescence (FIG. 4C) and near-infrared (FIG. 4D) in an animal model which is administered the bacterium-based microrobot.
Figure 4B:
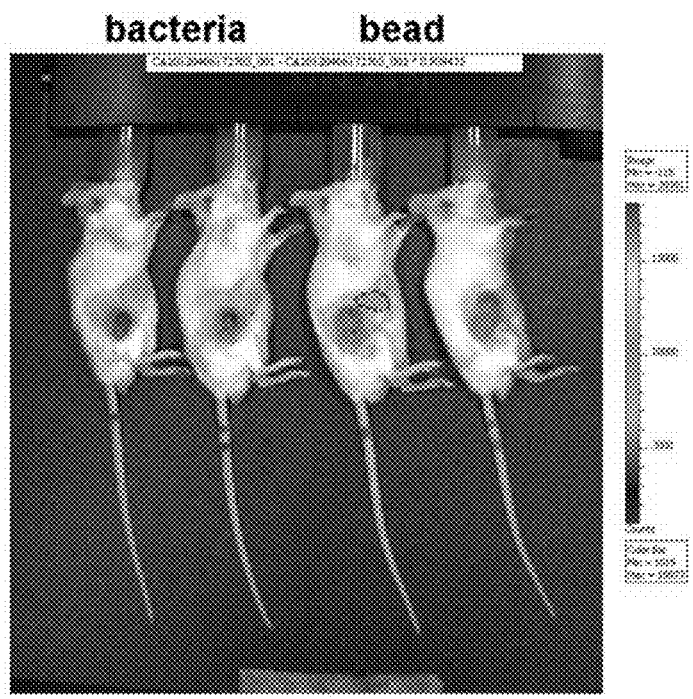
Figure 4C:
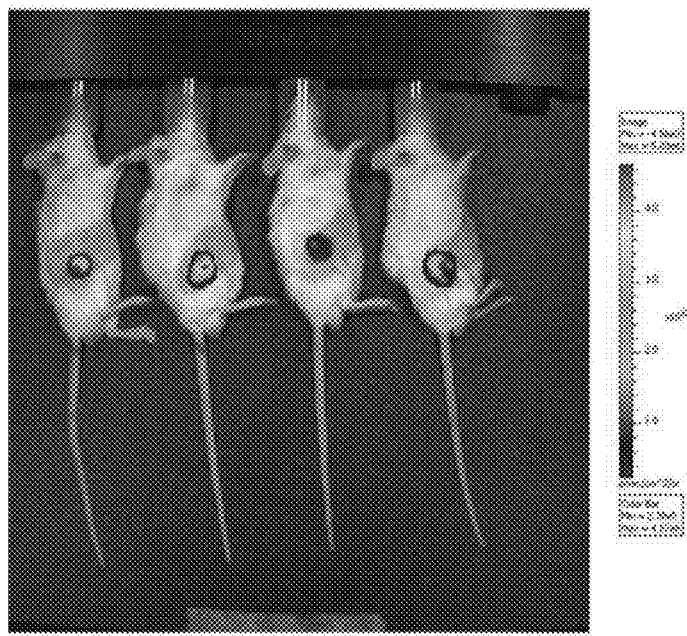
Figure 4D:
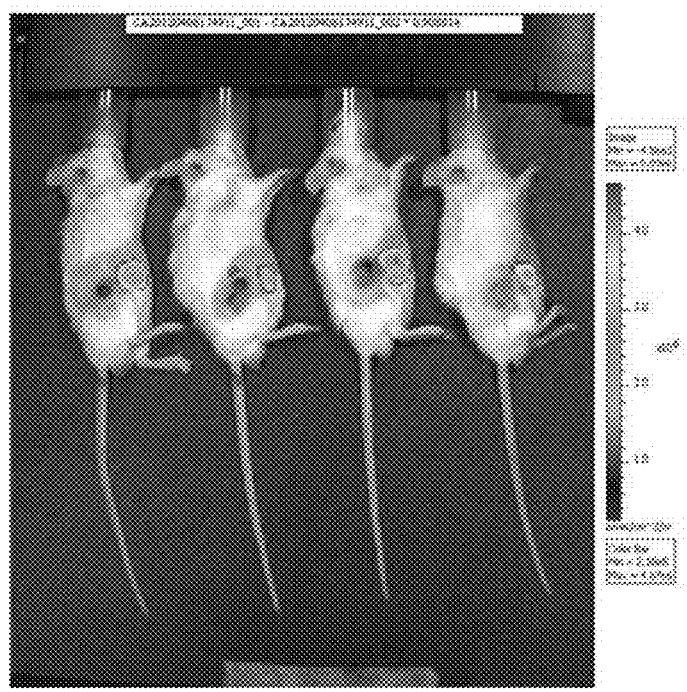
Figure 5A:
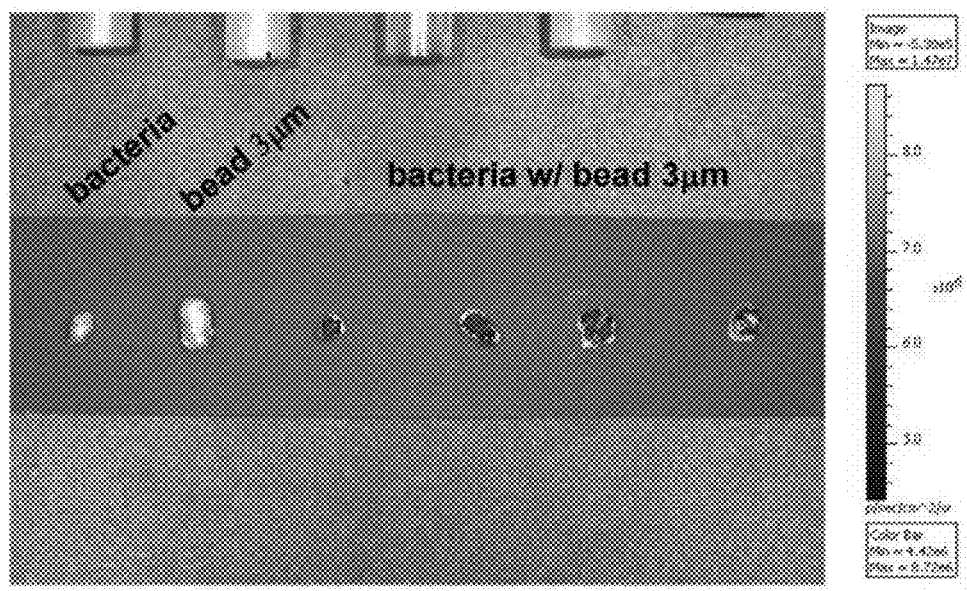
FIGS. 5A-5B are a series of photographs of a near-infrared image observed after a cancer tissue is extracted from the animal model which is administered with the bacteria (the *S. typhimurium* strain (ΔppGpp)) or the microbead, according to an example of the present invention (FIG. 5A) and an image showing results of the calculation of an amount of fluorescence generated per a region of interest (ROI) measured to quantify an amount of Cy5.5 fluorescence which was specifically generated in the cancer tissues of FIG. 5A (FIG. 5B).
Figure 5B:
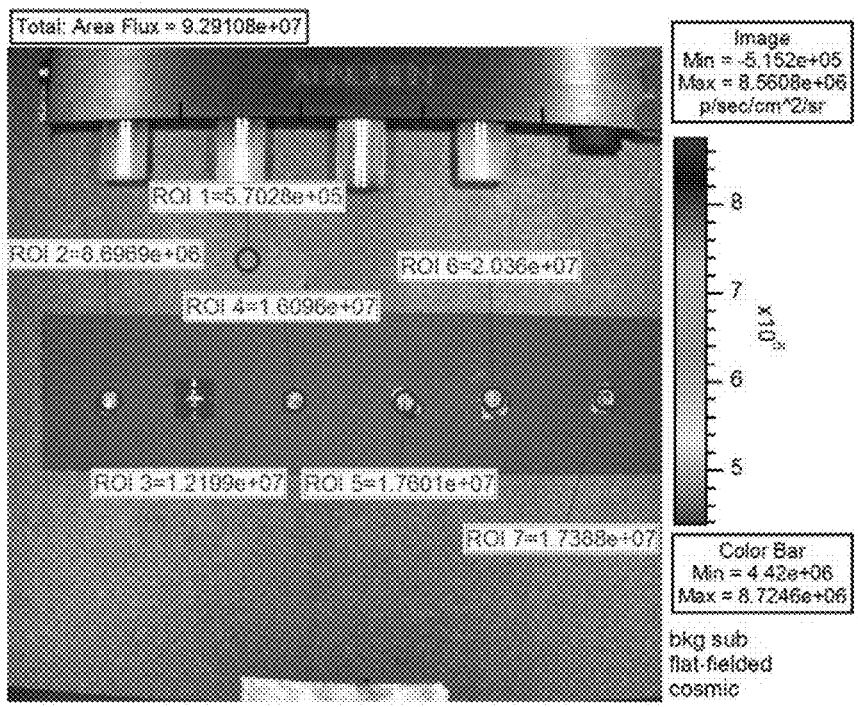

FIGS. 5A and 5B are a series of photographs of a near-infrared image observed after a cancer tissue is extracted from the animal model which is administered with the bacteria (the *S. typhimurium* strain (ΔppGpp)) or the microbead, according to an example of the present invention (FIG. 5A) and an image showing results of the calculation of an amount of fluorescence generated per a region of interest (ROI) measured to quantify an amount of Cy5.5 fluorescence which was specifically generated in the cancer tissues of FIG. 5A (FIG. 5B). It was verified that only the *S. typhimurium* strain (ΔppGpp), which forms the bacterium-based microrobot according to an example of the present invention, migrated to cancer tissue in FIG. 4. Therefore, whether the microbead migrates to cancer tissue in a bounded state with the *S. typhimurium* strain (ΔppGpp) was investigated after extracting cancer tissue. According to a result of observing cancer tissue of the animal model three days after administration, near-infrared was observed only in the bacterium-based microrobot, according to an example of the present invention, in a cancer tissue. The result proves that cancer cell-specific targeting can be accomplished by maintaining the binding between the microbead and the bacterium, which form the bacterium-based microrobot of the present invention, in vivo by means of streptavidin and biotin.

Figure 6A:
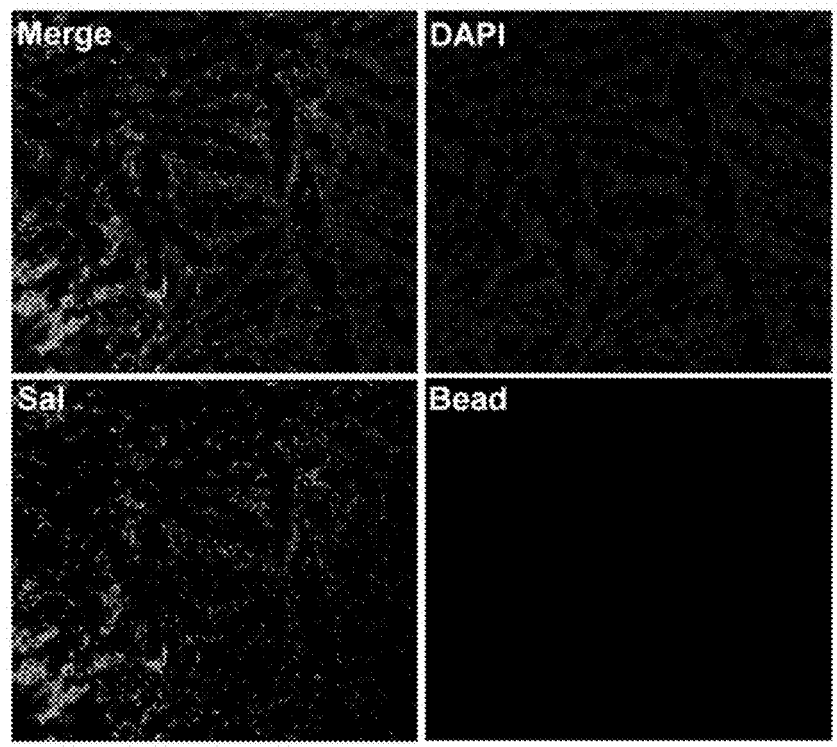
FIG. 6 is an image showing chemotoxis toward cancer using a immunostaining method of cancer tissue in an animal model at one day after administration of the bacteria (the *S. typhimurium* strain (ΔppGpp)) (FIG. 6A), the microbead (FIG. 6B), or the bacterium-based microrobot (FIG. 6C), according to an example of the present invention.
Figure 6B:
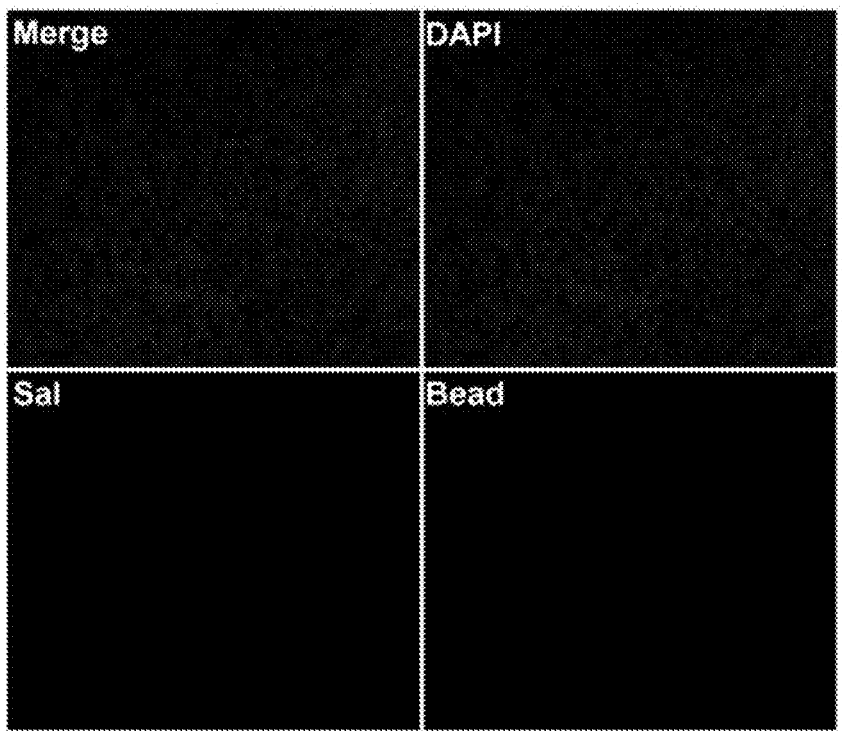
Figure 6C:
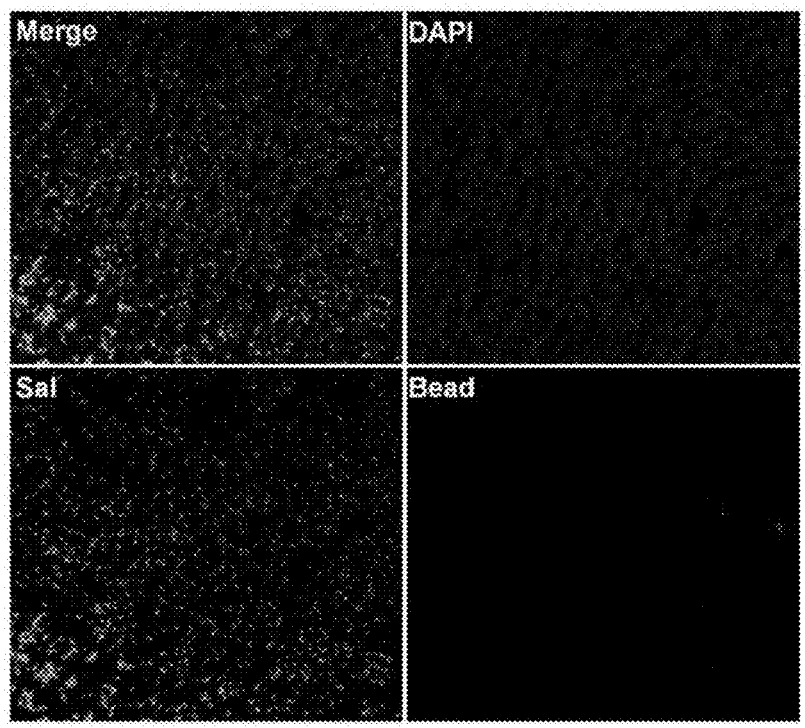

FIG. 6 is an image showing chemotaxis toward cancer using an immunostaining method of cancer tissue in an animal model at one day after administration of the bacteria (the *S. typhimurium* strain (ΔppGpp)) (FIG. 6A), the microbead (FIG. 6B), or the bacterium-based microrobot (FIG. 6C), according to an example of the present invention. According to results of staining cancer tissue using DAPI, GFP, and a Cy5.5 antibody, GFP expression was observed in the group administered with the *S. typhimurium* strain (ΔppGpp) (FIG. 6A), and fluorescence was not observed in the group administered with the microbead at all (FIG. 6B), whereas GFP and weak Cy5.5 fluorescence was observed in the group administered with the bacterium-based microrobot.

Figure 7A:
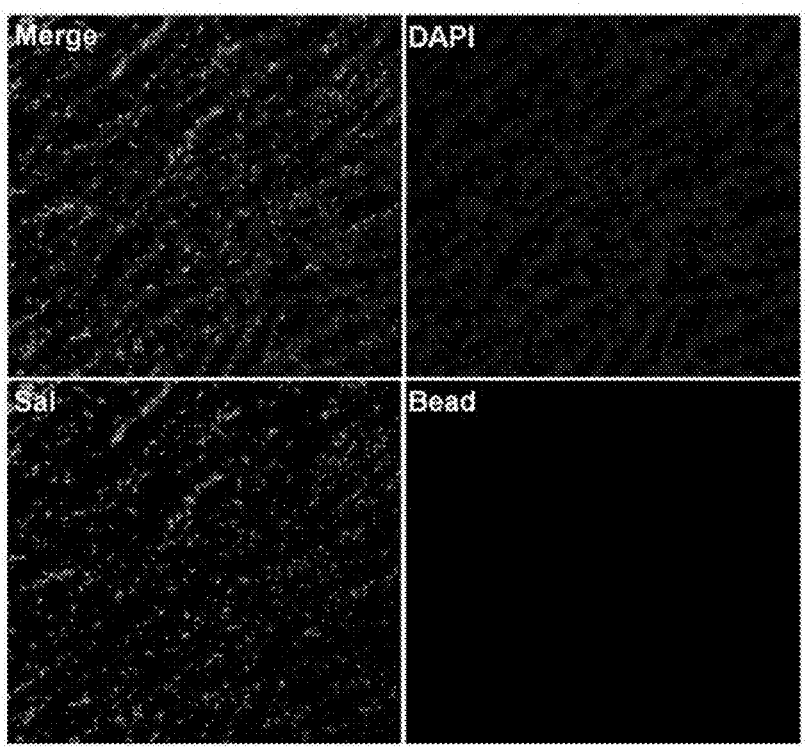
FIG. 7 is an image showing chemotaxis toward cancer using an immunostaining method of cancer tissue in an animal model at three days after administration of the bacteria (the *S. typhimurium* strain (ΔppGpp)) (FIG. 7A), the microbead (FIG. 7B), or the bacterium-based microrobot (FIG. 7C), according to an example of the present invention.
Figure 7B:
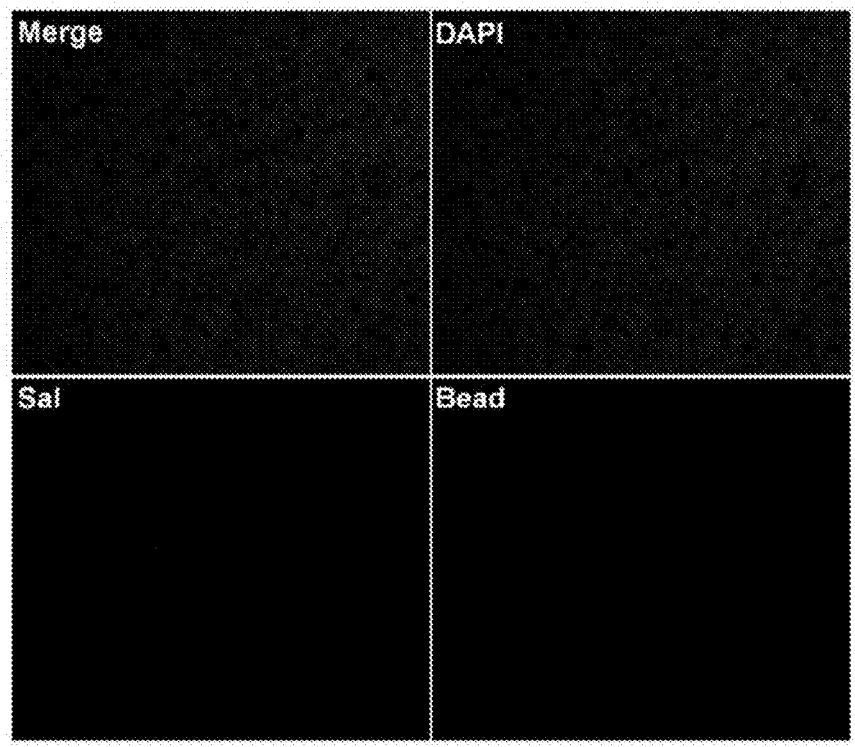
Figure 7C:
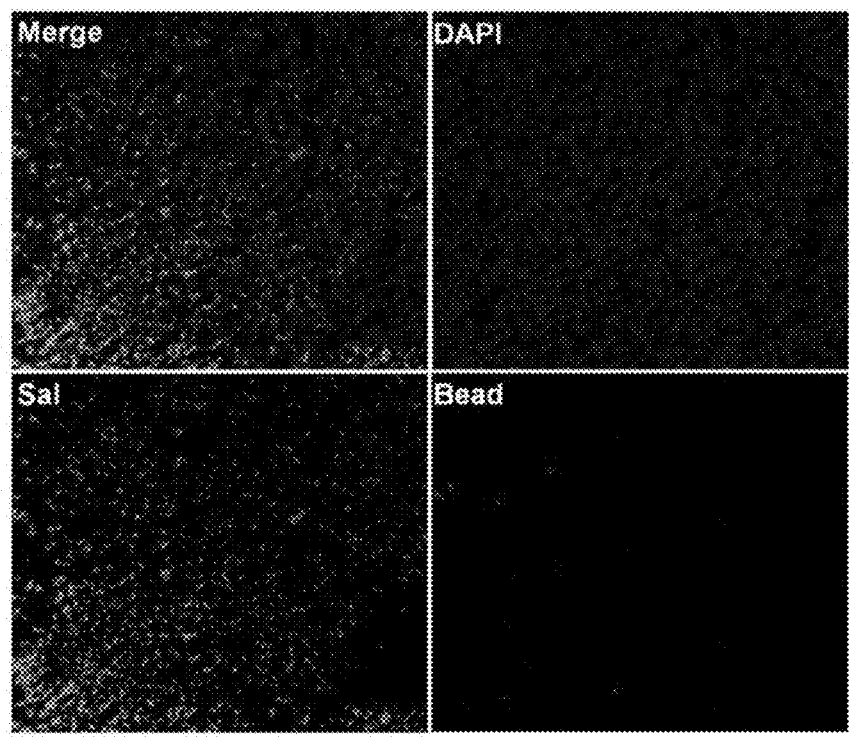

FIG. 7 is an image showing chemotaxis toward cancer using an immunostaining method of cancer tissue in an animal model at three days after administration of the bacteria (the *S. typhimurium* strain (ΔppGpp)) (FIG. 7A), the microbead (FIG. 7B), or the bacterium-based microrobot (FIG. 7C), according to an example of the present invention. The result was similar to that of FIG. 6, and stronger fluorescence of Cy5.5 was observed in the group administered the bacterium-based microrobot as the administration days goes by. The result proves that the binding between the *S. typhimurium* strain (ΔppGpp) and the microbead was maintained in vivo by means of streptavidin and biotin bond, and there is cancer-specific chemotaxis.

Figure 8A:
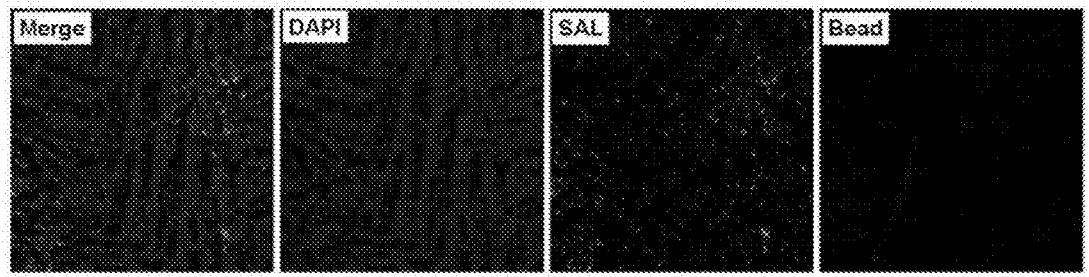
FIGS. 8A-8C are immunostaining photographs verifying whether the *S. typhimurium* strain (ΔppGpp), which forms the bacterium-based microrobot according to an example of the present invention (FIG. 8A), and the microbead are bounded or not in vivo, by using the z-stack function of a confocal microscopy (FIGS. 8B-8C)
Figure 8B:
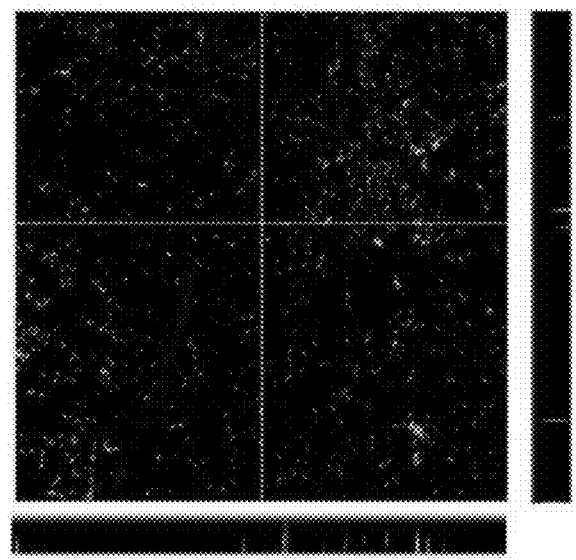
Figure 8C:
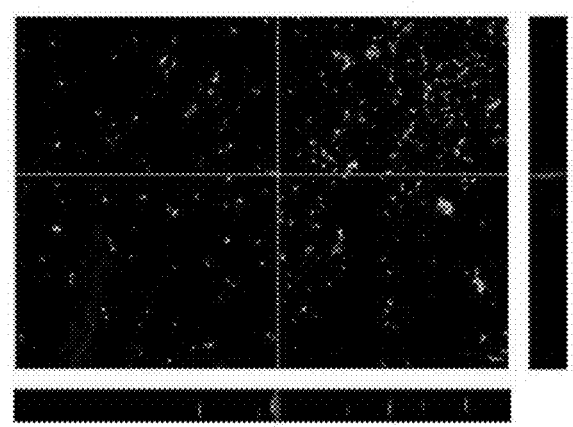

FIGS. 8A-8C are immunostaining photographs verifying whether the *S. typhimurium* strain (ΔppGpp), which forms the bacterium-based microrobot according to an example of the present invention (FIG. 8A), and the microbead are bounded in vivo, by using the z-stack function of a confocal microscopy (FIGS. 8B and 8C). After cancer tissue of the animal model administered with the bacterium-based microrobot, according to an example of the present invention, was extracted at the third day after administration and then immunostained, the cancer tissue was observed using the z-stack function of a confocal microscope. As a result, fluorescence of the *S. typhimurium* strain (ΔppGpp) and the microbead were observed at the same location.

Figure 9A:
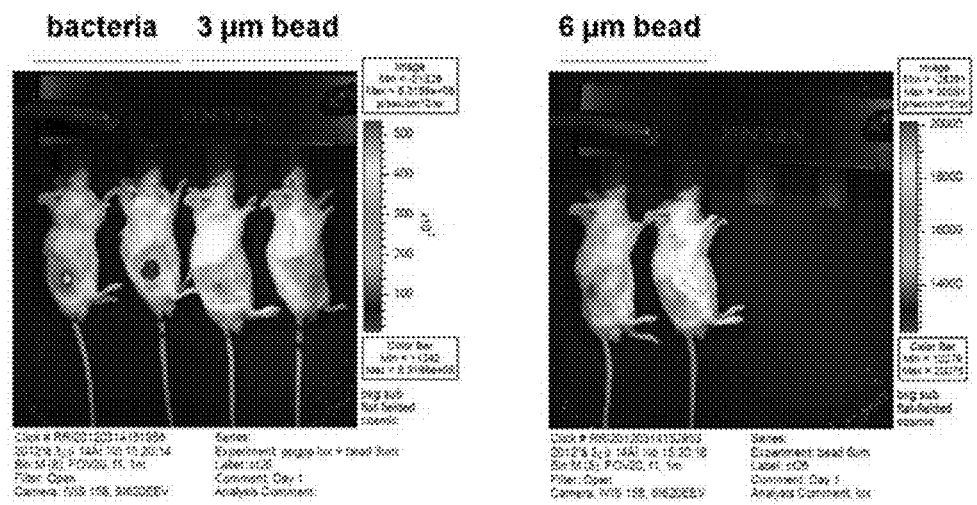
FIG. 9 is a photograph showing fluorescence (FIGS. 9A, B, and C), and near-infrared (FIGS. 9D, E, and F) in an animal model which is administered the *S. typhimurium* strain (ΔppGpp), a 3 μm or 6 μm of a microbead, and a microrobot produced by using the microbead, and showing near-infrared of cancer tissue extracted from the animal model (FIG. 9G), as results of comparing an anti-cancer effect of the bacterium-based microrobot, according to an example of the present invention, based on a size of the microbead.
Figure 9B:
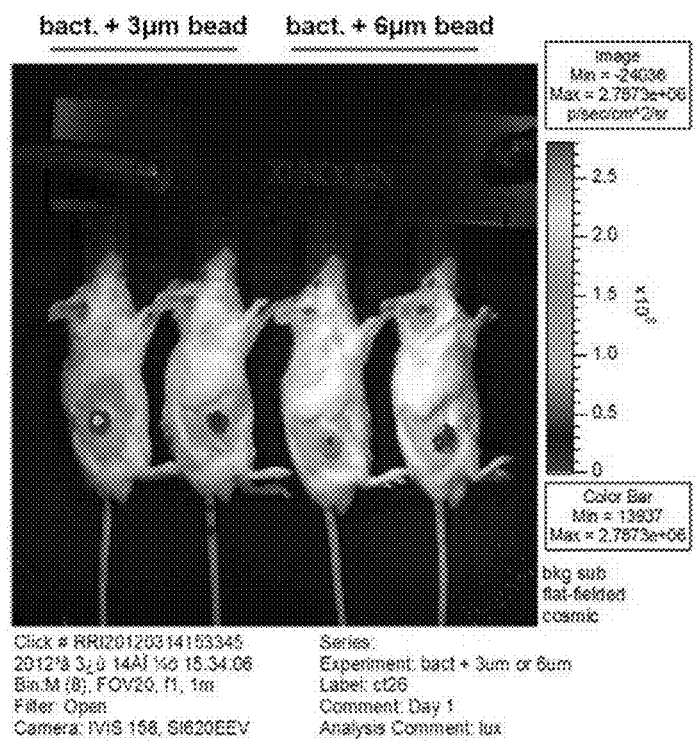
Figure 9C:
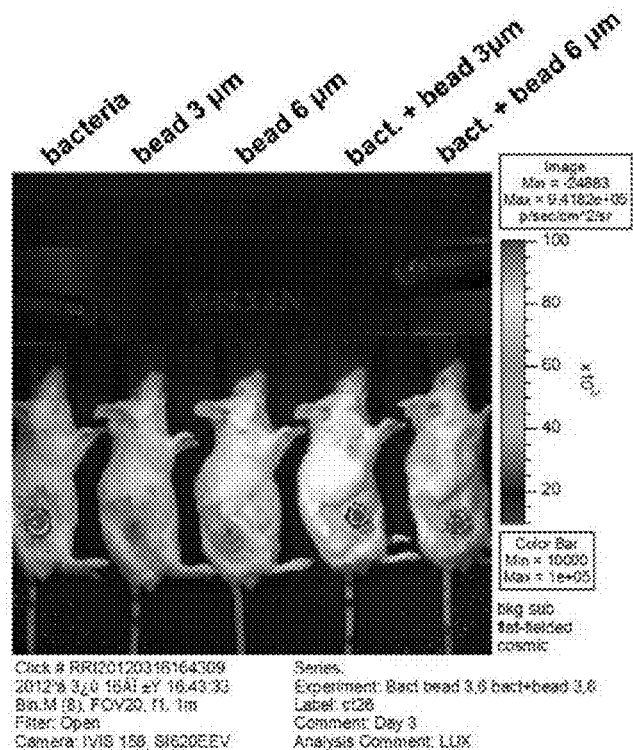
Figure 9D:
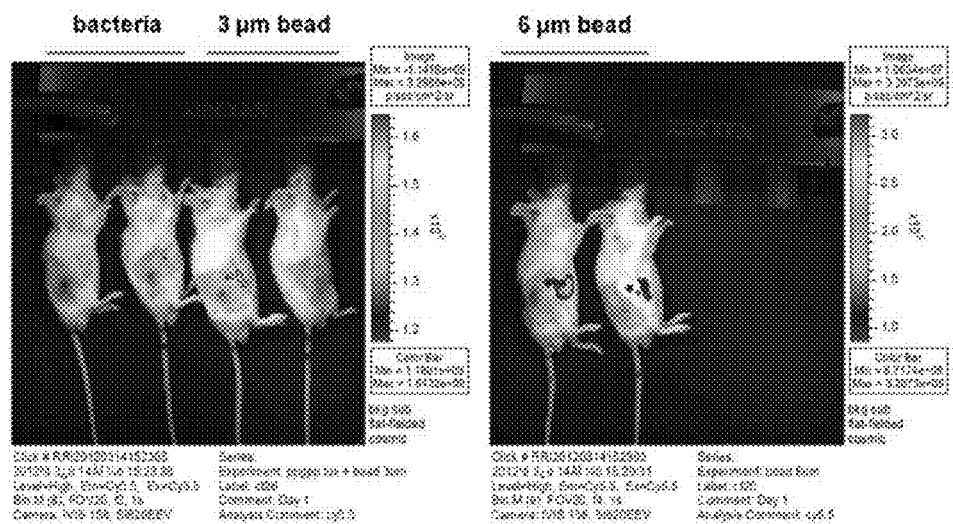
Figure 9E:
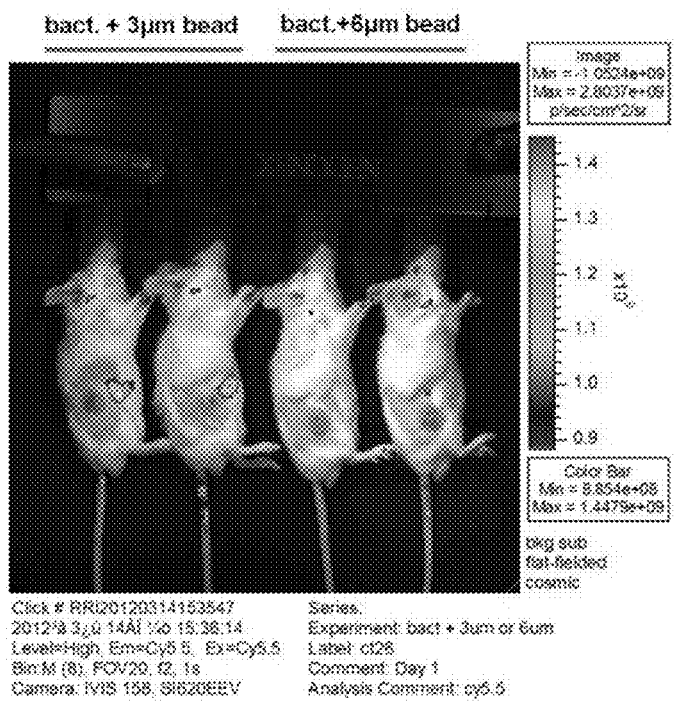
Figure 9F:
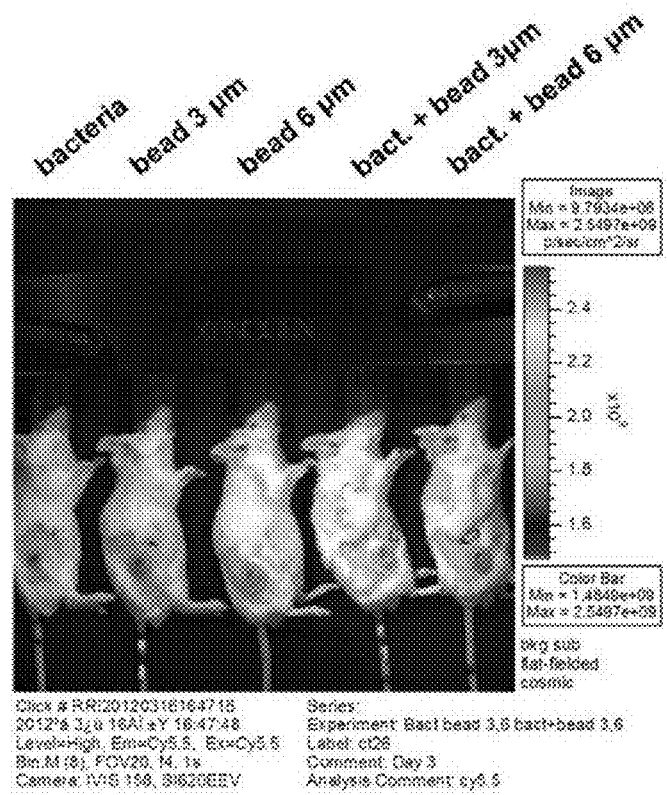
Figure 9G:
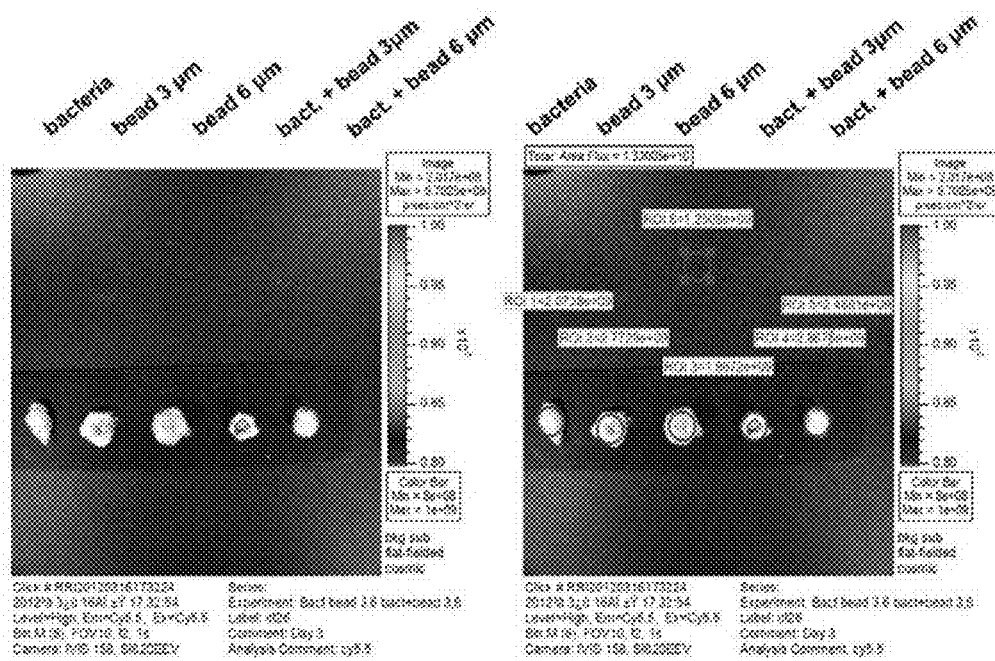

FIG. 9 is a photograph showing fluorescence (FIGS. 9A, B, and C), and near-infrared (FIGS. 9D, E, and F) in an animal model which is administered with the *S. typhimurium* strain (ΔppGpp), a 3 μm or 6 μm of a microbead, and a microrobot produced by using the microbead, and showing near-infrared of cancer tissue extracted from the animal model (FIG. 9G), as results of comparing an anti-cancer effect of the bacterium-based microrobot, according to an example of the present invention, based on a size of the microbead. To compare the anti-cancer effect of the microrobot based on a size of the bead, which forms the bacterium-based microrobot according to an example of the present invention, the microrobot, which was produced by using a microbead of 3 μm or 6 μm, was administered into the animal model of cancer and then motility toward cancer tissue and chemotaxis toward cancer were verified through luminescence and near-infrared. In the case of using the 3

μm microbead, luminescence and Cy 5.5 fluorescence were stronger. However, this fluorescence may cause interference to occur, and thus cancer tissue was extracted and observed directly. As a result, as shown in FIG. 9G, Cy5.5 fluorescence was observed only in the cancer tissue of the group into which the microrobot which is produced using the 3 μm microbead is injected. Thus, the result demonstrates that the anti-cancer effect may differ depending on the microbead which forms the microrobot.

Hereinafter, the present invention will be described in more detail with reference to examples and experimental examples. However, the present invention is not limited to examples and experimental examples below, and may be implemented in various forms different from each other. The below-described examples and experimental examples are merely provided for completing the present invention, and for completely enlightening contents of the present invention to a person skilled in the art.

Example 1: Production of Bacterium-Based Microrobot 1-1: Plasmids

A plasmid, pBAD-pelB-RLuc8 (pBP-Rluc8), was constructed according to the related art. More particularly, RLuc8, a specific mutant of *Renilla* luciferase, was produced in a combination of 8 favorable mutations, and then RLuc8 was inserted into a plasmid pBAD/Myc-His A (Invitrogen, Carlsbad, Calif.). A leader sequence, pelB, was linked to an N-terminal of a luciferase gene.

1-2: Bacterial Strains

An attenuated *S. typhimurium* strain (ΔppGpp), SHJ2037 (relA::cat, spoT::kn) which is used for the present experiment, is disclosed in the related thesis of the present inventor. The attenuated *S. typhimurium* strain (ΔppGpp), SHJ2037, which lacks in synthesis of guanosine 5'-diphosphate 3'-diphosphate (ppGpp) by deleting a relA gene and a spoT gene, was deposited in the gene bank of Korea Research Institute of Bioscience and Biotechnology, an international depositary authority, under a deposit number of KCTC 10787bP. *Salmonella* was cultured in LB medium (Difco Laboratories) including 50 μg/ml of kanamycin (Sigma) at 37° C. with vigorous aeration. The ΔppGpp strain was transformed by an in vivo luminescence reporter gene for in vivo luminescence imaging. A bacterial luciferase gene (lux) of *S. typhimurium*—Xen26 (Xenogen-Caliper) was introduced into the SHJ2037 strain using a P22HT-int transduction method. The strain was cultured in LB medium including 50 μg/ml of kanamycin. The plasmid pBAD-pelB-RLuc8 was introduced into the SHJ2037 strain through an electro-transformation method. A colony, which was grown on an LB agar plate including 20 μg/ml of ampicillin, was selected.

1-3: Microbeads

A surface of a carboxylated microbead was coated with streptavidin (eBioscience, Inc.), which is bound to Cy5.5 (eBioscience, Inc.), using a PolyLink Protein Coupling kit (Polysciences, Inc.). The fluorescence material has a limitation in penetrating skin due to weak energy, and thus the surface of microbead was coated with a Cy5.5 fluorescence material having a near-infrared wavelength band.

1-4: Bacterium-Based Microrobots

Then, 200 μg/ml of biotin (Thermo Scientific, Inc.) was incubated in the *S. typhimurium* strain (ΔppGpp) at 37° C. for one hour. The biotin is characterized in that it binds to OmpA, which is popularly present on a surface of a bacterial cell.

Then, bacteria cultured in the medium containing the biotin and the microbead coated with streptavidin were reacted by adding the coated bead to a bacterial medium at a ratio of $3 \times 10^7 : 1 \times 10^7$ (approximately 3:1) for 30 minutes thereby producing the bacterium-based microrobot.

Example 2: Production of Microfluidic Chip of 3-Chamber

A microfluidic chip was produced by referring to the previous invention of the present inventor (see Korean Patent Application No. 10-2011-0085207). The present inventor made a polydimethylsiloxane (PDMS) layer having a thickness of 5 mm on a slide glass, then formed channels having a width of 100 μm and a thickness of 100 μm between adjacent chambers after forming three circular chambers (diameter of 10 mm) in a row at intervals of 5 to 20 mm on the PDMS layer, wherein the circular chamber has a hole penetrating the top and the bottom of the chamber. Among the three chambers, a middle one is a chamber for loading a cell or a cell-based microrobot, and two chambers at both sides of the middle chamber are provided for loading a material to be analyzed.

Thereafter, the present inventors produced, as follows, a cell-containing hydrogel disc to be inserted into a chamber for loading a material to be analyzed which is formed in the microfluidic chip. An alginate hydrogel disc including a cell was produced by mixing and dissolving 2 g of alginate (Junsei Chemical Co., Japan) with 100 ml of phosphate buffered saline (PBS); mixing 1 ml of cell solutions having a concentration of $1 \times 10^6$ cells/ml of a colorectal cancer cell CT-26 (ATCC, Manassas, Va.), a breast cancer cell 4T1 (ATCC, Manassas, Va.) and a normal cell NIH3T3 (ATCC, Manassas, Va.) with 1 ml of 2% of alginate, respectively; and inducing gelation by dropping 100 μl of 1% alginate including the cell to a 40 mM of $CaCl_2$ solution.

Male Balb/c mice aged from 4 to 6 weeks (20 g, Samtaco, Gyeonggi-do, Korea) were used for an experiment. All animals were raised, used for experimentation, and euthanized according to the protocol, which is approved by an animal research center in Chonnam University, and the guide (Publication 85-23, revised in 1985) for the care and use of laboratory animal published from National Institute of Health (NIH). An animal model of cancer was produced by transplanting a cancer cell through a subcutaneous injection. A detailed method for producing the animal model is same as disclosed in the following reference (see Sheng-Nan Jiang et al., *Mol. Ther.*, 18(3): 635-642, 2010). A normal mouse into which a cancer cell was not transplanted was used as a control group of the animal model of cancer. The animal model of cancer had a feature in which cancer occurred on a right back region thereof, and thus a therapeutic effect of the bacterium-based microrobot, according to an example of the present invention, was investigated through the feature.

Experimental Example 1: Verification of Anti-Cancer Effect of *S. typhimurium* Strain (ΔppGpp)

An alginate hydrogel bead including a cell was produced by mixing and dissolving 2 g of alginate (Junsei Chemical Co., Japan) with 100 ml of phosphate buffered saline (PBS); mixing 1 ml of cell solutions having a colorectal cancer cell CT-26 (ATCC, Manassas, Va.), a breast cancer cell 4T1 (ATCC, Manassas, Va.) and 1 ml of cell solution having a concentration of $1 \times 10^6$ cells/ml, with the 1 ml of 2% alginate, respectively; and inducing gelation by dropping 100 μl of 1% alginate including the cell to a 40 mM of $CaCl_2$ solution. The bead was incubated for 24 hours at 37° C., and then the *S. typhimurium* strain (ΔppGpp) ($1\times10^6$ cfu/ml), which was used for the bacterium-based microrobot according to an example of the present invention, was loaded on the bead. After 6 hours, the cell was stained by being treated with EthD-1 having a final concentration of 4 μM. The EthD-1 selectively stains a dead cell in red.

As a result, it was observed that the CT-26 and 4T1 cells within the bead, which forms a spheroid by alginate, were stained red. This result proves a cancer cell killing effect of the *S. typhimurium* strain (ΔppGpp).

Experimental Example 2: Verification of Chemotaxis of Bacterium-Based Microrobot 2-1: Verification of Chemotaxis in 3-Chamber The following experiment was performed to verify whether or not the *S. typhimurium* strain (ΔppGpp), the anti-cancer effect of which has been verified in the experimental example 1, has chemotaxis toward a cancer cell selectively.

First, to verify whether the channel of the microfluidic chip produced in the example 2 operated appropriately, a blue dye was loaded on a chamber for loading a cell or a cell-based microrobot, and then a diffusion level of the blue dye was observed. As a result, as shown in FIG. 2A, a normal diffusion aspect was shown (see FIG. 2), that is, the concentration of the blue dye was decreased as the distance from the chamber for loading a cell or a cell-based microrobot was increased. This result proves that the microfluidic chip of the 3-chamber in the example 2 operates normally.

To verify chemotaxis of the *S. typhimurium* strain (ΔppGpp) toward a cancer cell in the chamber, the alginate hydrogel bead including a cell in a spheroid form was produced using alginate, and the cell existing in the hydrogel bead was stained through a 4',6-diamidino-2-phenylindole (DAPI) staining method (see FIG. 2b).

Thereafter, chemotaxis of the *S. typhimurium* strain (ΔppGpp) toward a cancer cell was investigated in the microfluidic chip in the 3-chamber. The microfluidic chip in the 3-chamber produced in the example 2 was put on a 100-mm cell culture dish. 20 ml of PBS was then poured to allow the microfluidic chip to be fully submerged and to prevent a bubble from being formed in the chamber and the channel. Then, the cell-containing hydrogel disc, which was produced in the example 2, was loaded on the chamber for loading a material to be analyzed, and fully submerged.

Thereafter, the *S. typhimurium* strain (ΔppGpp) or the bacterium-based microrobot ($1\times10^6$ cfu/ml), according to an example of the present invention, was loaded in the middle of the microchamer. Then, cell density was investigated at the same point for 20 minutes at intervals of 5 minutes. Bacterial density was measured through optical density using a computer program (ImageJ, USA) instead of directly counting the number. In the case of microrobot, the bead adhered to a bacterium was directly counted, and a moving distance was measured. The result was shown in FIG. 2D as a graph.

Resultantly, as shown in FIG. 2C to 2D, it is understood that the *S. typhimurium* strain (ΔppGpp) prefers a migration toward CT-26 and 4T1 which are cancer cells. It can be understood that the result was also same in the bacterium-based microrobot.

Experimental Example 3: Verification of Motility and Chemtaxis of Bacterium-Based Microrobot Toward Cancer in Animal Model To verify selective chemotaxis of the bacterium-based microrobot toward cancer and the anti-cancer effect of the bacterium-based microrobot, according to an example of the present invention, in vivo, following experiment was performed using an animal model.

3-1: Measurement of Luminescence and Near-Infrared of Model of Cancer

100 μl of the *S. typhimurium* strain (ΔppGpp), the microbead (3 μm), or the bacterium-based microrobot was respectively injected through tail vein of the animal model which was produced in the example 2. Luminescence and near-infrared using a Cy5.5 filter for three groups were measured by using an in-vivo imaging system (IVIS) at one day and three days after injection.

For bacterial in vivo luminescence imaging, a live mouse of the animal model, which was anesthetized, was put on a light-shielded chamber of the IVIS 100 (Xenogen-Caliper, Hopkinton, Mass.) which was equipped with a cooled charged couple detector (CCD) camera. A photon emitted from a luciferase-expressed bacterium was collected and integrated for one minute. A pseudo color image, which represents a count of a photon, was overlayed with a photograph of a mouse using a living image software v. 2.25 (Xenogen-Caliper, Hopkinton, Mass.).

Fluorescence and near-infrared were observed at the third day after administration of the *S. typhimurium* strain (ΔppGpp), the microbead, or the bacterium-based microrobot. As a fluorescence result observed in FIG. 4A, a group administered the microbead was coated with a near-infrared material only, and thus did not show luminescence; however, in the *S. typhimurium* strain (ΔppGpp), luminescence was observed in a cancer cell (FIG. 4A). Since, the *S. typhimurium* strain (ΔppGpp) may express a lux gene, a migration of the strain was verified through presence or absence of luminescence. Also, as a result observed using a near-infrared filter Cy5.5, the *S. typhimurium* strain (ΔppGpp) or the microbead was not observed in cancer tissue; however, a Cy5.5 signal was observed only in a group administered the bacterium-based microrobot, according to an example of the present invention. However, as observed in FIG. 4B, it was verified that, although a weak near-infrared signal was observed in liver and stomach regions of the mouse, this signal is auto-fluorescence which is generated by a feed of the mouse, not by the *S. typhimurium* strain (ΔppGpp) or the microbead.

3-2: Measurement of Near-Infrared of Cancer Tissue

As observed in the experimental example of 3-1, interference caused by auto-fluorescence occurred when near-infrared for the animal model was measured. Thus, it was verified whether the bacterium-based microrobot, according to an example of the present invention, was practically located in cancer tissue using a near-infrared filter Cy5.5, after extracting the cancer tissue from the animal model.

At three days after administration of the bacterium-based microrobot according to an example of the present invention, as similar to the experimental example 3-1, cancer tissue was extracted from a mouse of the animal model and near-infrared of extracted cancer tissue was observed using a near-infrared filter.

As a result, as shown in FIG. 5, Cy5.5 fluorescence was not observed in cancer tissue of the animal model, which was administered with the *S. typhimurium* strain (ΔppGpp) or the microbead. Whereas, Cy5.5 fluorescence was observed in cancer tissue of the animal model which was administered with the bacterium-based microrobot, according to an example of the present invention. The result proves that the microbead to which the *S. typhimurium* strain (ΔppGpp) was not bound did or have motility and cancer-directed property, however, the microbead to which the strain was bound (i.e. the bacterium-based microrobot) is capable of specifically targeting cancer tissue (see FIG. 5A).

Also, an amount of fluorescence generated per a certain area was measured to quantify an amount of Cy5.5 fluorescence which was specifically generated in cancer tissue extracted from an animal (see FIG. 5B).

3-3: Verification of Motility and Chemotaxis Toward Cancer of Bacterium-Based Microrobot Using Immunohistostaining Motility and chemotaxis, toward cancer, of the bacterium-based microrobot according to an example of the present invention was verified again using an immunostaining method.

In particular, tissue of an animal model was fixated through perfusion using 4% of paraformaldehyde, wherein the animal model was respectively administered with the *S. typhimurium* strain (ΔppGpp), the microbead or the bacterium-based microrobot, according to an example of the present invention, and lasted for one day or three days. Thereafter, cancer tissue was extracted and dehydrated by putting in PBS including 30% of sucrose, then cooled at −80° C. Subsequently, the tissue was cut into a piece with a thickness of 5 μm using cryomicrotome. Then, a cell nucleus of cancer tissue was stained blue using DAPI/Antifade (1:200; Invitrogen), and the bacterium was stained green using Alexa Fluor 488 chicken anti-rabbit (1:100, Invitrogen). The immunostaining result of the tissue was observed using a confocal optical microscopy (Olympus).

FIG. 6 shows an immunostaining result of cancer tissue at one day after administration as a photograph of tissue which is administered with bacteria (the *S. typhimurium* strain (ΔppGpp)) (see FIG. 6A), the microbead (see FIG. 6B), or the bacterium-based microrobot (see FIG. 6C). Green fluorescence was observed in cancer tissue of the group administered with the *S. typhimurium* strain (ΔppGpp), while red fluorescence was not observed in the group administered with the microbead. However, faint red fluorescence was observed in the group administered with the bacterium-based microrobot according to an example of the present invention (see FIG. 6).

Also, FIG. 7 shows an immunostaining result of cancer tissue of three days after administration. The same result as shown in FIG. 6 was observed, but red fluorescence of the microbead was slightly stronger than of the result obtained at the first day after administration (see FIG. 7). This result proves that the *S. typhimurium* strain (ΔppGpp) was strongly adhered to the surface of the microbead in vivo through a binding affinity between streptavidin and biotin, and the bacterium-based microrobot according to an example of the present invention was migrated to cancer tissue due to cancer tissue specific chemotaxis.

Experimental Example 4: Determination Binding of *S. typhimurium* Strain (ΔppGpp) and Microbead in Animal Model Subsequently, the present inventor verified again whether the *S. typhimurium* strain (ΔppGpp) is bound to the microbead using the z-stack function of a confocal microscopy.

First, a location in which green (*S. typhimurium* strain (ΔppGpp)) and red (microbead) co-existed, was arbitrarily selected (see FIG. 8A), and it was verified whether the location was same position of fluorescence using the z-stack function. As a result, as shown in FIGS. 8B and 8C, green and red fluorescence was observed at the same location. Thus, it is verified that the bacterium-based microrobot, according to an example of the present invention, existed in a strongly bounded state in cancer tissue (see FIGS. 8B and C).

Experimental Example 5: Anti-Cancer Effect Depending on Size of Microbead

An anti-cancer effect depending on a size of the microbead forming the bacterium-based microrobot according to an example of the present invention was compared. Specifically, selective chemotaxis toward a cancer cell and the anti-cancer effect were verified by using the bacterium-based microrobot which was produced using the 3 μm microbead and the 6 μm microbead, used in the experimental example 1 to 4.

5-1: Measurement of Luminescence and Near-Infrared of Animal Model of Cancer

Luminescence was measured using the same method as used in the experimental example 3. For comparison, an animal model injected with a bacterium-based microrobot which was produced by using the 6 μm microbead was further produced and compared to the bacterium-based microrobot of the 3 μm microbead.

Luminescence was measured by using in vivo imaging system (IVIS) at one day and three days after injection. As observation results of luminescence, it was observed that a luminescence level varied with the size of the microbead (see FIGS. 9B and 9C). Luminescence of the microrobot produced using the 3 μm microbead was stronger than that using the 6 μm microbead. As a control, luminescence was observed where the *S. typhimurium* strain (ΔppGpp), the 3 μm microbead, or the 6 μm microbead was respectively administered, as shown in FIG. 9A. Luminescence was observed in a mouse which was administered the *S. typhimurium* strain (ΔppGpp) (see FIG. 9A).

Near-infrared using a Cy5.5 filter was measured by using in vivo imaging system (IVIS) at one day and three days after injection. A stronger Cy5.5 signal was observed in the microrobot of the 3 μm microbead than the microrobot of the 6 μm microbead using near-infrared filter Cy5.5 (see FIGS. 9E and 9F). However, it was considered as auto-fluorescence since the observed signal was generated over liver and stomach regions.

5-2: Measurement of Near-Infrared of Cancer Tissue

Since, interference caused by auto-fluorescence was observed from the observation result of near-infrared, cancer tissue was extracted from an animal model at three days after injection, and near-infrared of the extracted cancer tissue was measured.

As a result, as shown in FIG. 9G, Cy5.5 fluorescence was observed in the animal model which was administered with the microrobot produced using the 3 μm microbead, and Cy5.5 fluorescence was not observed in the microrobot produced by using the 6 μm microbead. This result demonstrates that the size of the microbead affects motility of the microrobot with respect to cancer tissue.

In summary, the bacterium-based microrobot, according to an example of the present invention, is capable of specifically targeting cancer tissue due to chemotaxis of the *S. typhimurium* strain (ΔppGpp) toward cancer tissue, and also providing a therapeutic efficacy since the microrobot is bound in cancer tissue by applying a binding property between streptavidin and biotin.

As described above, according to examples of the present invention, it is possible to provide an anticancer effect by strongly binding a drug and/or a therapeutic bacterium to a microbead through binding affinity between streptavidin and biotin to thereby maintain the binding in vivo and allow the drug and/or the therapeutic bacterium to be migrated in a cancer specific way. Surely, the scope of the present invention is not limited by these effects.

Although the cancer tissue targeting bacterium-based microrobot and the uses thereof have been described with reference to the specific embodiments, they are not limited thereto. Therefore, it will be readily understood by those skilled in the art that various modifications and changes can be made thereto without departing from the spirit and scope of the present invention defined by the appended claims.

What is claimed is:

1. A drug delivery system for cancer tissue, comprising at least a mutant bacterium lack of an ability to synthesize guanosine 5'-diphosphate 3'-diphosphate (ppGpp), and a microbead encapsulating at least a drug, wherein at least a biotin is bound to a surface of the bacterium and a surface of the microbead is coated with streptavidin, and wherein the bacterium is bound to the microbead through an interaction between the biotin and the streptavidin, wherein the diameter of the microbead is 1 to 5 µm.

2. The drug delivery system of claim 1, the bacterium is *Salmonella, Clostridium, Bifidobacterium, E. coli, Yersinia enterocohtica, Listeria monocytogenies, Mycoplasma hominis*, or *Streptococcus*.

3. The drug delivery system of claim 1, wherein the cancer is any one selected from the group consisting of liver cancer, colorectal cancer, cervical cancer, renal cancer, gastric cancer, prostate cancer, breast cancer, brain tumor, lung cancer, uterine cancer, colon cancer, bladder cancer, hematologic malignancy and pancreatic cancer.

4. The drug delivery system of claim 1, wherein the drug is a marker gene, a chemical material, a peptide, a polypeptide, a nucleic acid, carbohydrate or lipid.

5. The drug delivery system of claim 4, wherein, the marker gene is a gene encoding a fluorescence protein or a luminescence protein, or a gene encoding a marker for nuclear medicine or MRI imaging comprising thymidine kinase of herpes simplex virus, a dopamine receptor, a somatostatin receptor, a sodium-iodide transporter, an iron receptor, a transferrin receptor, ferritin or an iron transporter (magA).

6. The drug delivery system of claim 4, wherein, the chemical material is at least one selected from doxorubicin, epirubicin, cisplatin, carboplatin, oxaliplatin, paclitaxel, docetaxel, 5-fluorouracil, cytarabine, gemcitabine, pentostatin, methotrexate, 7-ethyl-10-hydroxycamptothecin, trimetrexate, vinblastine, vincristine and dexamethasone.

7. The drug delivery system of claim 1, wherein, the microbead is produced by using a biodegradable/biocompatible polymer material.

8. The drug delivery system of claim 7, wherein, the biodegradable/biocompatible polymer material is one or more selected from chitosan, a salt and a derivative thereof; dextran and a derivative thereof; gum acacia; tragacanthin; hyaluronic acid, a salt and a derivative thereof; pectin, a salt and a derivative thereof; alginic acid, a salt and a derivative thereof; agar; galactomannan, a salt and a derivative thereof; xanthan, a salt and a derivative thereof; β-cyclodextrin, a salt and a derivative thereof; amylose (water soluble starch), a salt and a derivative thereof; glycol chitosan, a salt and a derivative thereof; carboxylmethyl cellulose (CMC), a salt and a derivative thereof; hydroxyethyl cellulose (HEC), a salt and a derivative thereof; hyroxypropyl methyl cellulose (HPMC), a salt and a derivative thereof; methyl cellulose, a salt and a derivative thereof; cellulose acetate phthalate, a salt and a derivative thereof; gelatin, a salt and a derivative thereof; promaine sulfate; poly(β-hydroxyethyl methacrylate) (PHEMA); polyacrylamide (PA); polyvunyl alcohol (PVA); polyacrylic acid (PAA); polyethylene gylcol (PEG); poly(ethylene oxide-b-propylene oxide) (PER-PPO); and polylyasine.

9. A pharmaceutical composition for treating cancer, comprising:
   (a) a pharmaceutically effective dose of the drug delivery system set forth in claim 1; and
   (b) a pharmaceutically acceptable carrier,
wherein the drug delivery system comprises a drug for treating cancer.

10. A composition for imaging cancer, comprising:
   (a) the drug delivery system set forth in claim 1; and
   (b) a pharmaceutically acceptable carrier.

11. A pharmaceutical composition for treating cancer, comprising:
   (a) a pharmaceutically effective dose of the drug delivery system set forth in claim 2; and
   (b) a pharmaceutically acceptable carrier,
wherein the drug delivery system comprises a drug for treating cancer.

12. A pharmaceutical composition for treating cancer, comprising:
   (a) a pharmaceutically effective dose of the drug delivery system set forth in claim 3; and
   (b) a pharmaceutically acceptable carrier,
wherein the drug delivery system comprises a drug for treating cancer.

13. A pharmaceutical composition for treating cancer, comprising:
   (a) a pharmaceutically effective dose of the drug delivery system set forth in claim 5; and
   (b) a pharmaceutically acceptable carrier,
wherein the drug delivery system comprises a drug for treating cancer.

14. A pharmaceutical composition for treating cancer, comprising:
   (a) a pharmaceutically effective dose of the drug delivery system set forth in claim 8; and
   (b) a pharmaceutically acceptable carrier,
wherein the drug delivery system comprises a drug for treating cancer.

* * * * *